United States Patent [19]

Hutson

[11] Patent Number: 5,629,336

[45] Date of Patent: May 13, 1997

[54] USE OF GLYCINE/NMDA RECEPTOR LIGANDS FOR THE TREATMENT OF DRUG DEPENDENCE AND WITHDRAWAL

[75] Inventor: Peter H. Hutson, Saffron Walden, England

[73] Assignee: Merck, Sharp & Dohme Ltd., Hoddesdon, England

[21] Appl. No.: 199,901

[22] Filed: Feb. 22, 1994

Related U.S. Application Data

[62] Division of Ser. No. 817,175, Apr. 20, 1992, abandoned.

[30] Foreign Application Priority Data

Apr. 26, 1991 [GB] United Kingdom .................. 9109007

[51] Int. Cl.$^6$ .......................... A61K 31/40; A61K 31/47
[52] U.S. Cl. .......................... 514/425; 514/300; 514/311; 514/312; 514/313; 514/314; 514/810; 514/812
[58] Field of Search .................. 514/425, 810, 514/812, 300, 311, 312, 313, 314, 423

[56] References Cited

FOREIGN PATENT DOCUMENTS

| 0303387 | 2/1989 | European Pat. Off. . |
| 0318091 | 5/1989 | European Pat. Off. . |
| 0362941 | 4/1990 | European Pat. Off. . |
| 0386839 | 9/1990 | European Pat. Off. . |
| 2231048 | 11/1990 | United Kingdom . |

OTHER PUBLICATIONS

Parks, T.N. et al., Brian Research 552 (1991) pp. 13–22.
Bistrow, L et al. The Glycine/Nmda Receptor Antagonists, R-(+)-HA966 and 5,7 Dichlorokynurenic Acid Attentuate Naltrexone-Precipitated Morphine Withdrawl in the Rat, British Journal of Pharmacology, vol. 112, May 1994.
Tricklebank, et al., Soc For Neuro., vol. 16, AB.200.1 (1990).
Singh, et al., Eur J. Pharm. vol. 186, p. 129 (1990).
Trujillo, et al., Science, vol. 251, pp. 85–87 (1991).
K. Rasmussen et al., Soc. Neurosci Abstract, vol. 16, p. 928 AB. #382.6, (1990).
K. Rasmussen et al., Eur. J. Pharmacol, vol. 197(1), pp. 9–16, (1991).
H. Koyungoglu et al., Int. J. Clin. Pharmacol Ther. Toxicol., vol. 28(4), pp. 147–152, (1990).
Stedman's Medical Dictionary, 24th Ed. p. 889, (1982).

Primary Examiner—Marianne M. Cintins
Assistant Examiner—M. Moezie
Attorney, Agent, or Firm—Robert J. North; Melvin Winokur

[57] ABSTRACT

Compounds capable of interacting with the strychnine-insensitive glycine modulatory site of the N-methyl-D-aspartate (NMDA) receptor are active in preventing or reducing dependence on dependence-inducing agents such as morphine, but lack the undesirable side-effects of agents hitherto employed for this purpose.

6 Claims, 4 Drawing Sheets

USE OF GLYCINE/NMDA RECEPTOR LIGANDS FOR THE TREATMENT OF DRUG DEPENDENCE AND WITHDRAWAL

This is a division of application Ser. No. 07/871,175, filed Apr. 20, 1992, now abandoned.

This invention relates to a new use for compounds capable of interacting with the strychnine-insensitive glycine modulatory site of the N-methyl-D-aspartate (NMDA) receptor. More particularly, the invention concerns the use of this class of compounds, referred to hereinafter as "glycine/NMDA receptor ligands", in the prevention or reduction of dependence on a dependence-inducing agent.

Glycine/NMDA receptor ligands are known, inter alia, from EP-A-0303387, EP-A-0318091, EP-A-0362941, EP-A-0386839 and GB-A-2231048. By virtue of their activity as specific antagonists of NMDA receptors, these compounds are stated to be useful in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Olivo-ponto-cerebellar atrophy, anoxia such as from drowning, spinal cord and head injury and poisoning by exogenous NMDA receptor agonists and neurotoxins. The compounds are also stated to be useful as anticonvulsant agents and muscle relaxants.

The psychological and physical dependence of certain individuals on dependence-inducing agents such as opiates, alcohol and other CNS depressants, psychostimulants or nicotine is a well-known and serious medical problem, having far-reaching social and economic implications. There is currently no single class of compounds suitable for the treatment of drug withdrawal syndromes. Current therapeutic strategies include: (a) transfer to less efficacious compounds (e.g. methadone); (b) treatment with the $\alpha_2$-adrenoceptor agonist, clonidine; and (c) treatment with anxiolytics, neuroleptics or sedatives. Clonidine has the useful property of attenuating the increased activity of noradrenergic neurons induced in the locus coerulus during morphine withdrawal, but the compound is also hypotensive and sedative. Recent work has suggested that the noncompetitive NMDA receptor antagonist, dizocilpine maleate (MK-801), reduces both morphine tolerance and the effects of withdrawal (Trujillo & Akil, *Science*, 1991, 251, 85–87), but only at doses that are known to induce marked behavioural stimulation and ataxia. Furthermore, repeated administration of MK-801 during exposure to morphine is required.

Although glycine/NMDA receptor ligands have certain functional properties, e.g. anticonvulsant effects, in common with compounds, such as MK-801, which act at the ion channel of the NMDA receptor complex, the two classes of compounds are nevertheless known to possess substantially different behavioural profiles (see, for example, Singh et al., *Eur. J. Pharmacol.*, 1990, 186, 129; and Tricklebank and Saywell, *Society for Neuroscience Abstracts*, 1990, 16, 200.1).

We have now found, indeed, that glycine/NMDA receptor ligands possess the beneficial activity of MK-801 in preventing or reducing dependence on dependence-inducing agents, but lack the undesirable side-effects. Thus, acute treatment with a glycine/NMDA receptor ligand potentiates morphine antinociception, and reduces both the behavioural and neurochemical responses to morphine withdrawal at doses devoid of stimulant, depressant or cardiovascular effects. Glycine/NMDA receptor ligands have been found to attenuate the increase in activity of noradrenergic neurons induced in the locus coeruleus during morphine withdrawal; and also reduce the acute effect of morphine in increasing the activity of the mesolimbic dopamine system, consistent with the attenuation of the rewarding effects of morphine. By contrast, MK-801 stimulates mesolimbic dopamine systems. In addition, multiple doses of MK-801 were utilised in the published studies, whereas glycine/NMDA receptor ligands have been found to be effective after a single dose.

The present invention accordingly provides the use of a glycine/NMDA receptor ligand for the manufacture of a medicament for the prevention or reduction of dependence on a dependence-inducing agent.

The invention also provides a method for the prevention or reduction of dependence on a dependence-inducing agent, which method comprises administering to a patient in need of such treatment an effective amount of a glycine/NMDA receptor ligand.

Continuous treatment with high doses of opiates such as morphine renders these agents progressively less effective as analgesics. Furthermore, sudden withdrawal of the analgesic can induce intense behavioural and physical symptoms that severely limit the ease with which drug intake can be reduced. Combined administration of a glycine/NMDA receptor ligand with the opiate (a) restores analgesic efficacy; (b) reduces the rewarding effect of the drug; and (c) prevents the appearance of withdrawal symptoms on cessation of treatment with the opiate. Similar syndromes of varying degrees of intensity occur on withdrawal from chronic treatment with benzodiazepine receptor agonists, cocaine derivatives, nicotine and alcohol. Thus, glycine/NMDA receptor ligands are of use in the treatment of withdrawal and dependence phenomena deriving from chronic exposure to a number of psychoactive drugs.

In general, for example if the dependence-inducing agent is alcohol or nicotine, or a narcotic drug, the glycine/NMDA receptor ligand will be administered subsequent to ingestion of the dependence-inducing agent. Alternatively, however, if the dependence-inducing agent is an otherwise beneficial pharmaceutical compound such as an opiate analgesic, e.g. morphine, it may be administered concomitantly with, or even prior to, administration of the glycine/NMDA receptor ligand. Indeed, it has been found in particular that glycine/NMDA receptor ligands are capable of potentiating the analgesic effect of a dependence-inducing analgesic agent such as morphine.

In a further aspect, therefore, the present invention provides a product containing an otherwise beneficial dependence-inducing agent and a glycine/NMDA receptor ligand as a combined preparation for simultaneous, separate or sequential use in the therapy of a disorder against which the dependence-inducing agent is beneficial. Suitably the otherwise beneficial dependence-inducing agent mentioned above is an analgesic compound. Preferably, this compound is morphine.

In a still further aspect, the invention provides a pharmaceutical composition comprising a glycine/NMDA receptor ligand in association with a dependence-inducing agent. In a suitable embodiment, the dependence-inducing agent in the aforementioned pharmaceutical composition is nicotine.

The glycine/NMDA receptor ligands of use in the present invention may be any glycine/NMDA receptor ligand known from the art. Examples of suitable glycine/NMDA receptor ligands of use in this invention include those classes of compounds described in EP-A-0303387, EP-A-0318091, EP-A-0362941, EP-A-0386839 and GB-A-2231048.

A particular glycine/NMDA receptor ligand of use in the invention is the R-(+) isomer of 3-amino-1-hydroxypyrrolidin-2-one, otherwise known as (+)-HA-966, having the structure and absolute stereochemistry depicted in formula I:

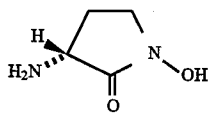

or a pharmaceutically acceptable salt thereof.

Alternatively, the glycine/NMDA receptor ligand may be a compound of formula II or a pharmaceutically acceptable salt thereof:

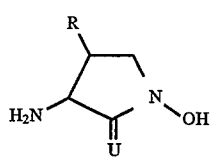

such that both the substituents R and —NH$_2$ are in a cis-configuration;

wherein R represents a hydrocarbon group and U represents oxygen or sulphur.

Amongst the compounds of formula II, a particular glycine/NMDA receptor ligand of use in the present invention is that wherein R is methyl and U is oxygen, i.e. cis-3-amino-1-hydroxy-4-methylpyrrolidin-2-one, otherwise known as L-687,414.

Another category of glycine/NMDA receptor ligands of use in the invention comprises the compounds of formula III and pharmaceutically acceptable salts thereof:

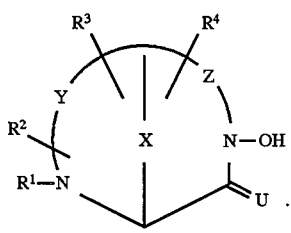

wherein

R$^1$, R$^3$ and R$^4$ independently represent hydrogen or hydrocarbon;

R$^2$ represents hydrogen, hydrocarbon, halogen, —OR$^a$, —SR$^a$, —NR$^a$R$^b$, —NR$^a$COR$^b$, —NR$^a$CO$_2$R$^b$, —NR$^a$SO$_2$R$^b$, —NR$^i$CTNR$^a$R$^b$, —CO$_2$R$^a$ or —CONR$^a$R$^b$;

U represents oxygen or sulphur;

X, Y and Z independently represent a bond or a group of formula —(CH$_2$)$_m$— or —(CH$_2$)$_q$CH=CH(CH$_2$)$_r$—, provided that X, Y and Z do not simultaneously each represent a bond;

R$^a$, R$^b$ and R$^i$ independently represent hydrogen or hydrocarbon;

T represents oxygen, sulphur or a group of formula =N.E;

E represents hydrocarbon or an electron-withdrawing group;

m is an integer from 1 to 4; and q and r independently represent zero or 1.

Specific compounds of formula III of use in the present invention include the following:

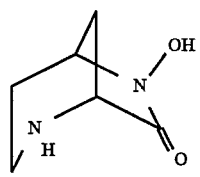

2,6-diaza-6-hydroxy-7-oxobicyclo[3.2.1]octane

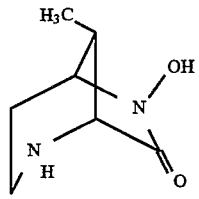

2,6-diaza-6-hydroxy-8-endo-methyl-7-oxobicyclo[3.2.1]octane and pharmaceutically acceptable salts thereof.

Also suitable as a glycine/NMDA receptor ligand of use in the present invention may be a 4-oxo-1,4-dihydroquinoline having a 2-acidic group or a group convertible thereto in vivo; or a pharmaceutically acceptable salt thereof.

The benzo moiety in the dihydroquinoline ring system may be substituted or unsubstituted. Suitable substituents include a hydrocarbon group or a functional substituent such as hydroxy, halogen, amino, carboxy, alkoxy, alkylthio, trifluoromethyl or cyano.

The acidic group at the 2-position of the dihydroquinoline nucleus may represent for example a carboxy or carboxyalkyl group or a group which is convertible to a carboxy or carboxyalkyl group; hydroxamic acid; tetrazolyl; or tetrazolylalkyl.

Specifically, the 4-oxo-1,4-dihydroquinoline derivative mentioned above may be a compound of formula IV:

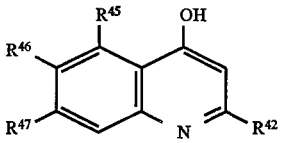

or a pharmaceutically acceptable salt thereof, wherein R$^{42}$ represents an acidic group, or a group which is convertible thereto in vivo, and R$^{45}$, R$^{46}$ and R$^{47}$ independently represent hydrogen, hydrocarbon, hydroxy, halogen, amino, carboxy, alkoxy, alkylthio, trifluoromethyl or cyano.

It will be appreciated that the 4-oxo compound of formula IV will in general be in tautomeric equilibrium with the 4-hydroxy compound of formula IVA:

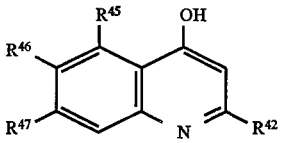

although under standard conditions the 4-oxo isomer of formula IV will significantly predominate.

Amongst the compounds of formula IV, a particular glycine/NMDA receptor ligand of use in the present invention is that wherein R$^{42}$ is carboxy, R$^{45}$ is iodo, R$^{46}$ is hydrogen and R$^{47}$ is chloro, i.e. 7-chloro-5-iodo-4-oxo-1,4-dihydroquinoline-2-carboxylic acid, otherwise known as 7-chloro-5-iodokynurenic acid.

A further class of glycine/NMDA receptor ligands of use in the invention comprises the compounds of formula V and pharmaceutically acceptable salts thereof:

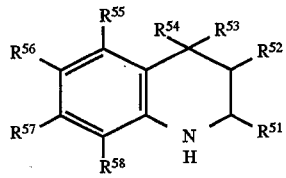

(V)

wherein $R^{51}$ represents an acidic group or a group which is convertible thereto in vivo;

$R^{52}$ represents hydrogen or hydrocarbon;

$R^{53}$ represents hydrogen, hydrocarbon, —OR$^a$, —SR$^a$, —NR$^a$R$^b$, —NR$^a$COR$^b$, —NR$^a$CO$_2$R$^b$, —NR$^a$SO$_2$R$^b$, —NR$^i$CTNR$^a$R$^b$, —CO$_2$R$^a$ or —CONR$^a$R$^b$;

$R^{54}$ represents hydrocarbon, —OR$^a$, —SR$^a$, —NR$^a$R$^b$, —NR$^a$COR$^b$, —NR$^a$CO$_2$R$^b$, —NR$^a$SO$_2$R$^b$, —NR$^i$CTNR$^a$R$^b$, —CO$_2$R$^a$ or —CONR$^a$R$^b$; or $R^{53}$ and $R^{54}$ together with the intervening carbon atom represent carbonyl (C=O), thiocarbonyl (C=S), imino (C=N.R$^a$), oximino (C=N.OR$^a$), or a 3- to 8-membered ring containing from zero to 4 heteroatoms selected from oxygen, nitrogen, sulphur and phosphorus;

$R^{55}$, $R^{56}$, $R^{57}$ and $R^{58}$ independently represent hydrogen, hydrocarbon, halogen, cyano, trifluoromethyl, nitro, —OR$^a$, —SR$^a$, —NR$^a$R$^b$ or —CO$_2$R$^a$; and $R^a$, $R^b$, $R^i$, T and E are as defined above with reference to formula III.

The acidic groups $R^{42}$ and $R^{51}$ in the compounds of formulae IV and V above may represent carboxy, carboxyalkyl, or a group convertible thereto in vivo such as an in vivo hydrolysable ester or amido group. Such groups may be represented by the moiety —(CH$_2$)$_v$COB wherein v is zero, 1 or 2, and B is OR$^r$ or NR$^p$R$^q$, where R$^r$ is hydrogen, hydrocarbon or an in vivo hydrolysable ester residue and R$^p$ and R$^q$ are independently hydrogen, hydrocarbon or in vivo hydrolysable amido residues. Examples of suitable in vivo hydrolysable ester and amido groups for $R^{42}$ and $R^{51}$ include those which break down readily in the human body to leave the parent acid or its salt. Typical ester and amido groups $R^{42}$ and $R^{51}$ of this type are illustrated in EP-A-0303387 and EP-A-0386839.

Alternatively, the acidic groups $R^{42}$ and $R^{51}$ may represent any other group which can provide an anion, for example a hydroxamic acid derivative of formula —CONR$^p$OH or —CONH.OR$^p$ where R$^p$ is as defined above; or tetrazolyl or tetrazolyl(C$_{1-3}$)alkyl; or a derivative of any of these groups which is hydrolysable thereto in vivo.

The term "hydrocarbon" as used herein includes straight-chained, branched and cyclic groups, including heterocyclic groups, containing up to 18 carbon atoms, suitably up to 15 carbon atoms, and conveniently up to 12 carbon atoms. Suitable hydrocarbon groups include C$_{1-6}$ alkyl, C$_{1-6}$ alkenyl, C$_{2-6}$ alkynyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl and heteroaryl (C$_{1-6}$)alkyl.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups. A particular aryl(C$_{1-6}$)alkyl group is benzyl.

Suitable heterocycloalkyl groups include piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, thienyl, benzthienyl, imidazolyl, oxadiazolyl and thiadiazolyl groups. Particular heteroaryl groups are pyridyl and oxadiazolyl.

The hydrocarbon group may in turn be optionally substituted by one or more groups selected from C$_{1-6}$ alkyl, adamantyl, phenyl, halogen, C$_{1-6}$ haloalkyl, trifluoromethyl, hydroxy, C$_{1-6}$ alkoxy, aryloxy, keto, C$_{1-3}$ alkylenedioxy, nitro, cyano, carboxy, C$_{1-6}$ alkoxycarbonyl, C$_{1-6}$ alkoxycarbonyl(C$_{1-6}$)alkyl, C$_{1-6}$ alkylcarbonyloxy, optionally substituted arylcarbonyloxy, C$_{1-6}$ alkylcarbonyl, optionally substituted arylcarbonyl, C$_{1-6}$ alkylthio, C$_{1-6}$ alkylsulphinyl, C$_{1-6}$ alkylsulphonyl, amino, mono- or di(C$_{1-6}$)alkylamino, C$_{1-6}$ alkylcarbonylamino and C$_{1-6}$ alkoxycarbonylamino.

When the group E represents an electron-withdrawing group, this group is suitably cyano, nitro, —COR$^a$, —CO$_2$R$^a$ or —SO$_2$R$^a$, in which R$^a$ is as defined above.

The term "halogen" as used herein includes fluorine, chlorine, bromine and iodine, especially chlorine.

The compounds of use in this invention generally have at least one asymmetric centre and often more than one; and can therefore exist both as enantiomers and as diastereoisomers. In particular, those compounds of formula III, possessing an unsymmetrical azabicyclic ring system, may exist as exo and endo diastereoisomers. It is to be understood that the invention relates to the use of all such isomers and mixtures thereof.

Suitable pharmaceutically acceptable salts of the glycine/NMDA receptor ligands of use in this invention include acid addition salts which may, for example, be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid or phosphoric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the invention also contemplates salts thereof, preferably non-toxic pharmaceutically acceptable salts thereof, such as the sodium, potassium and calcium salts thereof.

Particularly preferred glycine/NMDA receptor ligands of use in the present invention include (+)-HA-966 and L-687, 414, and pharmaceutically acceptable salts thereof.

When administered alone, the glycine/NMDA receptor ligands of use in this invention can be administered orally, parenterally or rectally at a daily dose of about 0.01 to 100 mg/kg of body weight, preferably about 0.1 to 10 mg/kg, and may be administered on a regimen of 1 to 4 times a day.

The pharmaceutical composition according to the present invention may conveniently be administered orally, rectally or parenterally. For oral administration, the formulation may conveniently be in the form of tablets, pills, capsules, powders or granules; for parenteral administration, sterile parenteral solutions or suspensions may conveniently be utilised; and for rectal administration, the formulation may conveniently be in the form of suppositories.

The compositions may be formulated by conventional methods known in the pharmaceutical art.

When administered in combination, the dependence-inducing agent and the glycine/NMDA receptor ligand may be presented in a ratio which is consistent with the manifestation of the desired effect. In particular, the ratio by weight of the dependence-inducing agent to the glycine/NMDA receptor ligand will suitably be approximately 1 to 1. Preferably, this ratio will be between 0.001 to 1 and 1000 to 1, and especially from 0.01 to 1 to 100 to 1.

The dependence-inducing agent will suitably be administered in conventional doses. Thus, for example, morphine may be administered to hospitalised patients at a dose of 10 mg s.c. or i.p. in order to elicit an analgesic effect. In this context, a suitable dosage level for the glycine/NMDA receptor ligand is about 0.01 to 50 mg/kg/day, preferably about 0.05 to 25 mg/kg/day and especially about 0.01 to 10 mg/kg/day. The pharmaceutical composition of the invention may conveniently be administered on a regimen of 1 to 4 times per day.

The compounds of formulae I to V as defined above may be prepared by the methods described in EP-A-0318093, EP-A-0362941, GB-A-2231048, EP-A-0303387 and EP-A-0386839 respectively.

Specific aspects of the invention will now be described with reference to the accompanying drawings in which:

BRIEF DESCRIPTION OF THE DRAWINGS

FIG. 3 shows the effect of (+)-HA-966 on morphine-induced dopamine synthesis.

Figure 1:
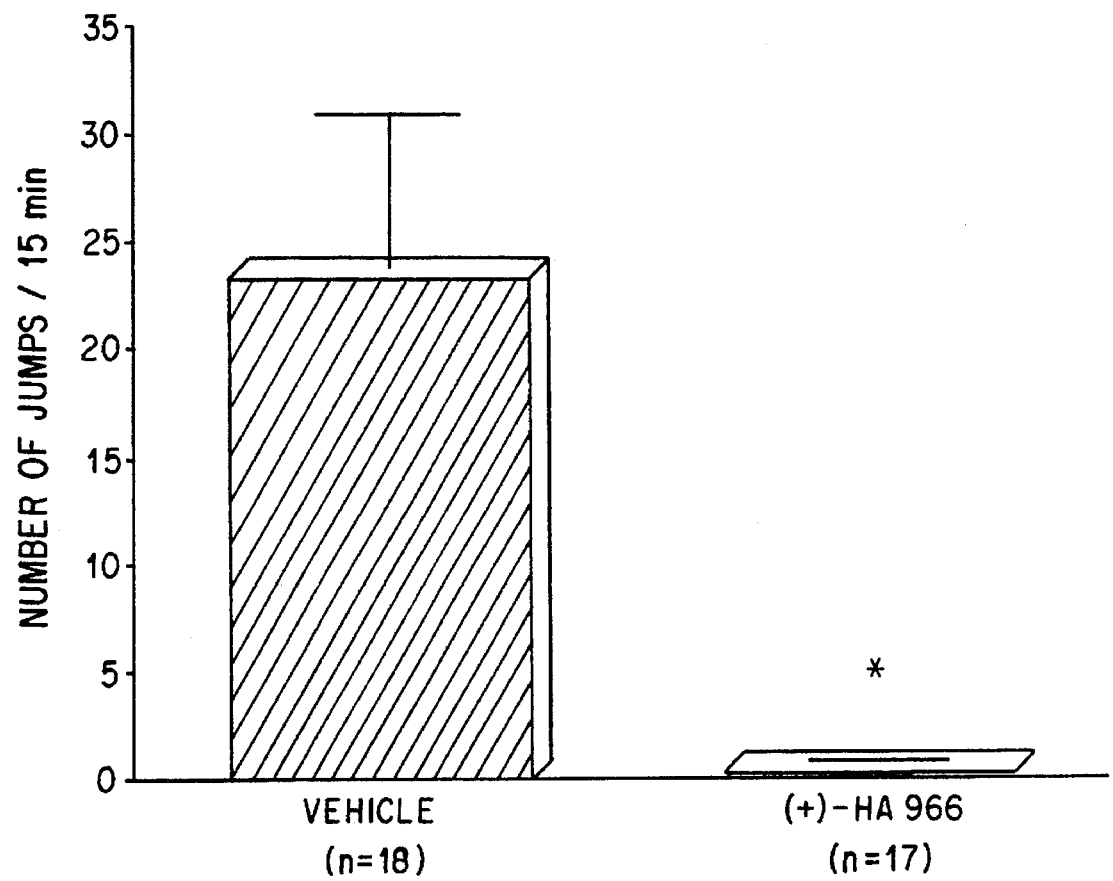
FIG. 1 shows the effect of (+)-HA-966 on naloxone-induced escape jumping in morphine-dependent mice.

Effect of (+)-HA-966 on Naloxone Induced Escape Jumping in Morphine-Dependent Mice Male BKTO mice (30–35 g) were treated with morphine.HCl (231 mg/kg; 718 αmol/kg s.c.) at 10:00, 14:00 and 17:00 h on day 1 and 70 mg/kg (215 αmol/kg s.c.) at the same times on days 2 and 3. On the fourth day, mice received morphine (215 αmol/kg s.c.) at 09:00 h. At 13:00 h mice were injected with either saline (10 ml/kg i.p.) or (+)-HA-966 (100 mg/kg, 862 αmol/kg i.p.) and placed in perspex cages for 30 min at which time they were injected with naloxone.HCl (0.5 mg/kg, 1.5 αmol/kg i.p.) and replaced in the cages. The number of escape jumps in 15 min was recorded, and the results obtained are plotted in FIG. 1, in which * denotes p<0.01 in the Mann-Whitney U test. From FIG. 1 it can be seen that naloxone induced pronounced jumping in saline pretreated mice, but this effect was significantly blocked by (+)-HA-966.

Figure 2:
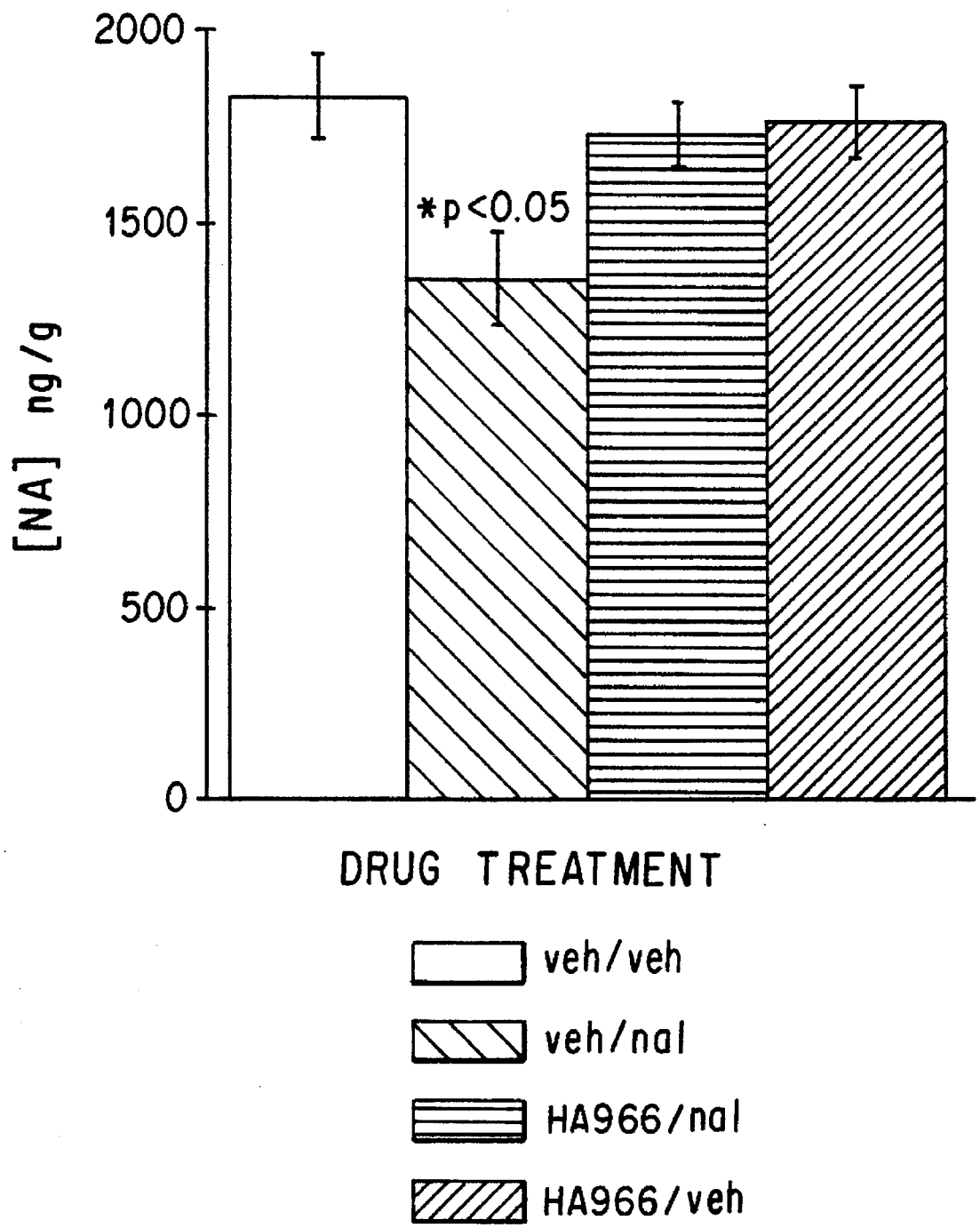
FIG. 2 shows the effect of (+)-HA-966 on the naloxone-induced decrease in locus coeruleus noradrenaline content in morphine-dependent rats.
Figure 3A:
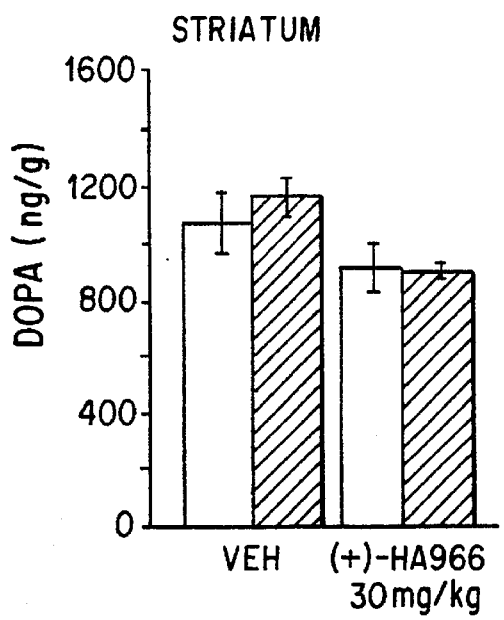
FIG. 3A and FIG. 3B show that a 30 mg/kg (3A) and 100 mg/kg (3B), (+)-HA-966 i.p. was without effect on DOPA in the striatum region of the brain in animals given only saline (vehicle), and that morphine did not increase the concentration of DOPA in the striatum. The results are depicted in which the blank bars indicate vehicle-treated mice and the hatched bars indicate morphine-treated mice.
Figure 3B:
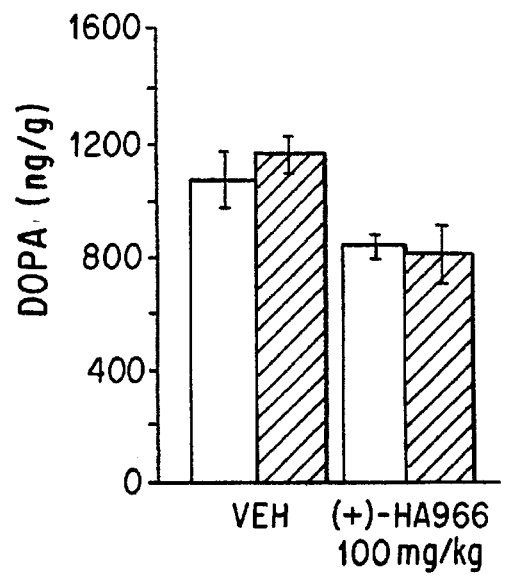
Figure 3C:
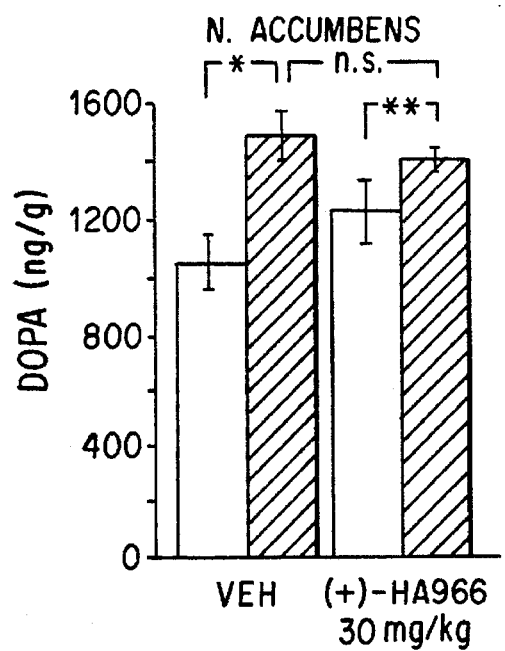
FIG. 3C and FIG. 3D show that at 30 mg/kg (3C) and 100 mg/kg (3D), (+)-HA-966 i.p. was without effect on DOPA in the nucleus accumbens region of the brain in animals given only saline (vehicle), but dose-dependently antagonised the increase in DOPA content induced in the nucleus accumbens by admininstration of morphine. In the Figure, * and ** denote p<0.01 and p<0.05, respectively, and "n.s." denotes no significant difference. The results are depicted in which the blank bars indicate vehicle-treated mice and the hatched bars indicate morphine-treated mice.
Figure 3D:
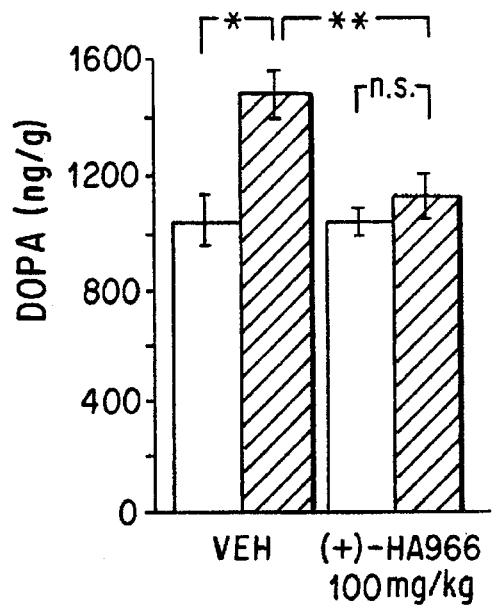

Effect of (+)-HA-966 on Noradrenaline Concentration in the Locus Coeruleus of Morphine-Dependent Rats Given Naloxone Male Sprague Dawley rats were made dependent on morphine following the method described by Collier et al., Nature, 1972, 237, 220–223. Rats were injected subcutaneously with morphine.HCl (150 mg/kg, 467 αmol/kg in 10 ml of 50:50 saline:Freunds incomplete adjuvant). 24 h later they were treated with either saline (1 ml/kg i.p.) or (+)-HA-966 (30 mg/kg, 258 αmol/kg i.p.) followed 30 min later by naloxone.HCl (2 mg/kg i.p., 6 αmol/kg i.p.). Animals were killed 15 min later, their brains removed and the locus coeruleus dissected. Noradrenaline (NA) concentration was determined using HPLC with electrochemical detection. The results obtained are plotted in FIG. 2. From FIG. 2 it is apparent that, in morphine-dependent rats, naloxone caused a significant decrease of locus coeruleus noradrenaline concentration when compared to morphine-treated rats given saline. Pretreatment with (+)-HA-966, meanwhile, had no effect on NA concentration in vehicle-treated rats, but prevented the naloxone-induced decrease of NA concentration. These data suggest that (+)-HA-966 prevents the change of noradrenaline metabolism in the locus coeruleus induced by naloxone in morphine-dependent rats.

In a further experiment, male Sprague Dawley rats were given morphine 150 mg/kg s.c. and 24 h later treated with vehicle (veh, 0.9% NaCl) or (+)-HA-966 (30 mg/kg i.p.) followed after 30 min by naloxone (nal, 2 mg/kg i.p.) or veh. The rats were observed for 2 min, 7–9 min after injection of naloxone or vehicle and the duration of mouth movements (including teeth chattering, teeth grinding, vacuous chewing and oral tremor) determined. Animals were also scored for the presence or absence of irritability (vocalisation on grasping around the abdomen), wet dog shakes, ejaculations and penile grooming. The results obtained from these tests are displayed in Table 1 below.

TABLE 1

| | Number of Animals Showing: | | | | |
|---|---|---|---|---|---|
| | Mouth Movements (sec) | Irritability | Wet Dog Shakes | Ejaculations | Penile Grooming |
| veh/veh | 1.5 ±0.7 | 0/6 | 0/6 | 0/6 | 0/6 |
| veh/(+)-HA-966 | 0.25 ±0.25 | 0/6 | 0/6 | 0/6 | 0/6 |
| veh/nal | 38.5 ±8.5 | 6/6 | 3/6 | 3/6 | 3/6 |
| (+)-HA-966/nal | 6.48* ±3.3 | 2/6* | 1/6 | 2/6 | 0/6 |

*p < 0.05 vs. rats given morphine and naloxone.

From Table 1 above, it will be noted that naloxone induced a marked mouth movement response which was significantly attenuated by (+)-HA-966. (+)-HA-966 also significantly reduced irritability, but other components of the syndrome were not sufficiently intense for clear antagonism by (+)-HA-966 to be seen.

Effect of (+)-HA-966 on the Increase In Dopamine Synthesis in Mouse Nucleus Accumbens Induced by Acute Treatment with Morphine Male BKTO mice (30–35 g) were injected i.p. with (+)-HA-966 (30 or 100 mg/kg) or saline, 20 min before the injection of morphine.HCl (10 mg/kg) and followed 20 min later by administration of the aromatic amino acid decarboxylase inhibitor, NSD 1015. After a further 30 min, mice were killed and the concentration of DOPA determined in the striatum and nucleus accumbens by HPLC with electrochemical detection. The results obtained are depicted in FIG. 3, in which the blank bars indicate vehicle-treated mice and the hatched bars indicate morphine-treated mice. The data were analysed by 2-way ANOVA followed by Tukey test. In FIG. 3, * and ** denote p<0.01 and p<0.05 respectively, and n.s. denotes no significant difference. As will be apparent from FIG. 3, morphine did not increase the concentration of DOPA in the striatum, but increased the level in the nucleus accumbens. (+)-HA-966 was without effect on DOPA in both striatum and nucleus accumbens of animals given only saline, but dose-dependently antagonised the increase in DOPA content induced in the nucleus accumbens by administration of morphine.

Effect of Acute Administration of (+)-HA-966 on Morphine-induced Analgesia

Figure 4:
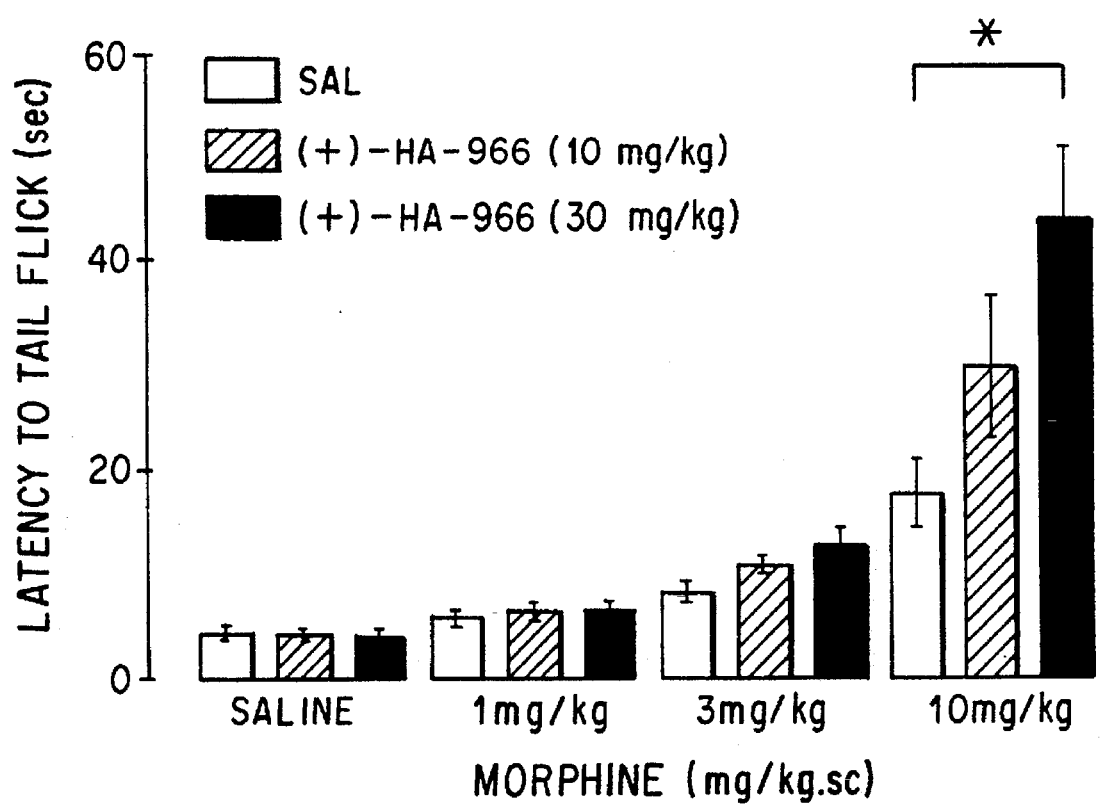
FIG. 4 shows the effect of pretreatment with (+)-HA-966 on morphine-induced analgesia.

Male Sprague Dawley rats (130–150 g) were pretreated with (+)-HA-966 (10 or 30 mg/kg i.p.) or saline (1 ml/kg) 30 minutes prior to subcutaneous injection of morphine (1, 3, 10 mg/kg) or saline (1 ml/kg). Analgesia was then determined 30 minutes later by recording the latency to remove the tail from water at 50° C., and the results obtained are recorded in FIG. 4, in which * denotes p<0.05. From FIG. 4 it will be observed that, under these conditions, the latency to tail removal in saline-treated rats was 4.4±0.6 seconds (mean±SEM) and was not significantly different from rats pretreated with (+)-HA-966, 10 mg/kg (4.2±0.5 sec) or 30 mg/kg (4±0.6 sec). In contrast, pre-treatment with morphine dose-dependently enhanced the tail removal latency, a dose of 10 mg/kg significantly increasing the latency to 17.6±3.3 sec. Whilst (+)-HA-966 itself did not induce an analgesic response, the increased tail removal latency seen following morphine (10 mg/kg) administration was dose-dependently and significantly enhanced in rats pretreated with (+)-HA-966 (10, 30 mg/kg i.p.).

I claim:

1. A method for the treatment of dependence on an opiate dependence-inducing agent, which method comprises administering to a patient in need thereof an effective amount of a compound, or a pharmaceutically acceptable salt thereof, said compound selected from the group consisting of (a), (b), (c), (d) and (e), being:

(a) R-(+)-3-amino-1-hydroxypyrrolidin-2-one;

(b) a compound of formula II:

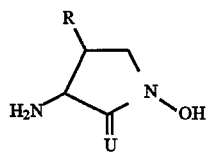

(II)

wherein the substituents R and —NH$_2$ are in a cis-configuration;

wherein R represents a hydrocarbon group, selected from the group consisting of: $C_{1-6}$alkyl, $C_{2-6}$alkenyl, $C_{2-6}$alkynyl, $C_{3-7}$cycloalkyl, $C_{3-7}$cycloalkyl($C_{1-6}$)alkyl, aryl, aryl($C_{1-6}$)alkyl, $C_{3-7}$heterocycloalkyl, $C_{3-7}$heterocycloalkyl($C_{1-6}$)alkyl, heteroaryl and heteroaryl($C_{1-6}$)alkyl;

wherein: aryl is phenyl or naphthyl; heterocycloalkyl is piperidyl, piperazinyl or morpholinyl; heteroaryl is pyridyl, quinolyl, isoquinolyl, pyridazinyl, pyrimidinyl, pyrazinyl, pyranyl, furyl, benzofuryl, thienyl, benzthienyl, imidazolyl, oxadiazolyl or thiadiazolyl;

and wherein said hydrocarbon group can be optionally substituted by one or more groups selected from $C_{1-6}$alkyl, adamantyl, phenyl, halogen, $C_{1-6}$haloalkyl, trifluoromethyl, hydroxy, $C_{1-6}$alkoxy, aryloxy, keto, $C_{1-3}$alkylenedioxy, nitro, cyano, carboxy, $C_{1-6}$alkoxycarbonyl, $C_{1-6}$alkoxycarbonyl($C_{1-6}$)alkyl, $C_{1-6}$alkylcarbonyloxy, arylcarbonyloxy, $C_{1-6}$alkylcarbonyl, arylcarbonyl, $C_{1-6}$alkylthio, $C_{1-6}$alkylsulphinyl, $C_{1-6}$alkylsulphonyl, amino, mono- or di($C_{1-6}$)alkylamino, $C_{1-6}$alkylcarbonylamino and $C_{1-6}$alkoxycarbonylamino;

and U represents oxygen or sulphur;

(c) cis-3-amino-1-hydroxy-4-methylpyrrolidin-2-one;

(d) 4-oxo-1,4-dihydroquinoline having a 2-acidic group or a group convertible thereto in vivo; and (e) 7-chloro-5-iodo-4-oxo-1,4-dihydroquinoline-2-carboxylic acid.

2. The method according to claim 1 wherein the compound administered is R-(+)-3-amino-1-hydroxypyrrolidin-2-one or a pharmaceutically acceptable salt thereof.

3. The method according to claim 1 wherein the compound administered is a compound of formula II or a pharmaceutically acceptable salt thereof:

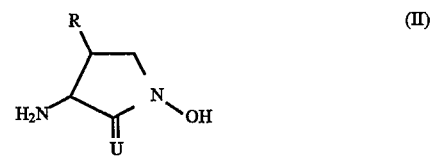

(II)

such that both the substituents R and —NH$_2$ are in a cis-configuration;

wherein R represents a hydrocarbon group and U represents oxygen or sulphur.

4. The method according to claim 3 wherein the compound administered is cis-3-amino-1-hydroxy-4-methylpyrrolidin-2-one or a pharmaceutically acceptable salt thereof.

5. The method according to claim 1 wherein the compound administered is a 4-oxo-1,4-dihydroquinoline having a 2-acidic group or a group convertible thereto in vivo; or a pharmaceutically acceptable salt thereof.

6. The method according to claim 5 wherein the compound administered is 7-chloro-5-iodo-4-oxo-1,4-dihydroquinoline-2-carboxylic acid or a pharmaceutically acceptable salt thereof.

* * * * *